United States Patent [19]

Honzawa

[11] Patent Number: 5,019,416

[45] Date of Patent: May 28, 1991

[54] METHOD OF MODIFYING THE SURFACE OF A PARTICLE COMPRISING A MAGNETIC PARTICLE

[75] Inventor: Katsu Honzawa, Shizuoka, Japan

[73] Assignee: Hamamatsu Photonics K. K., Shizuoka, Japan

[21] Appl. No.: 497,200

[22] Filed: Mar. 22, 1990

[30] Foreign Application Priority Data

Mar. 23, 1989 [JP] Japan .................................. 1-71350

[51] Int. Cl.⁵ .............................................. B05D 3/14
[52] U.S. Cl. ..................................... 427/47; 427/127; 427/407.1; 427/443.2
[58] Field of Search ....................... 427/47, 127, 407.1, 427/443.2

[56] References Cited

U.S. PATENT DOCUMENTS

| | | | |
|---|---|---|---|
| 1,407,067 | 2/1922 | Johnson | 427/47 |
| 4,272,510 | 6/1981 | Smith et al. | 427/47 |
| 4,777,145 | 10/1988 | Luotola et al. | 436/526 |

FOREIGN PATENT DOCUMENTS

| | | |
|---|---|---|
| 0125995 | 11/1984 | European Pat. Off. |
| WO86/04684 | 8/1986 | PCT Int'l Appl. |
| WO86/06493 | 11/1986 | PCT Int'l Appl. |

OTHER PUBLICATIONS

Wu, Jengyue et al., "Two-Dimensional Reaction Solvents: Surfactant Bilayers in the Formation of Ultrathin Films" Langmuir 1987, 3, pp. 53–57.

Waite, Kay V. et al., "Immunoradiometric Assay With Use of Magnetizable Particles: Measurement of Thyrotropin in Blood Spots to Screen for Neonatal Hypothyroidism" Clinical Chemistry, vol. 32, No. 10 1986, pp. 1966–1968.

Kang, J. et al., "A Highly Sensitive Immunoenzymometric Assay Involving Common-Capture Particles and Membrane Filtration" Clinical Chemistry, vol. 32, No. 9, 1986, pp. 1682–1686.

Primary Examiner—Bernard Pianalto
Attorney, Agent, or Firm—Finnegan, Henderson, Farabow, Garrett, and Dunner

[57] ABSTRACT

A particle comprising a magnetic particle is placed in a liquid having a monomolecular film formed on its surface. Then, the particle is pulled up by means of a pair of electromagets facing each other with the air-liquid interface present therebetween so that the particle passes through the interface. As a result, a monomolecular coat is formed on the surface of the particle. A monomolecular built-up coat is formed by repeating the above procedure predetermined times.

10 Claims, 1 Drawing Sheet

METHOD OF MODIFYING THE SURFACE OF A PARTICLE COMPRISING A MAGNETIC PARTICLE

BACKGROUND OF THE INVENTION

The present invention relates to a method of modifying the surface of a particle comprising a magnetic particle. For example, it relates to the method of modifying the surface of a bead for use in bead agglutination to detect an antigen-antibody reaction.

Bead agglutination is one of the techniques to detect an antigen-antibody reaction used in immunoassays. In bead agglutination, fine particles such as plastic beads having antibodies adhered to their surfaces are used in carrying out reaction with associated antigens and the degree of agglutination of beads is measured to detect and identify very small amounts of antigen and antibody. In the conventional method of bead agglutination, a polystyrene bead is used as a plastic bead but its affinity for antibody is too low to have them adhere to each other in sufficient amount to ensure precise detection and identification.

SUMMARY OF THE INVENTION

An object, therefore, of the present invention is to provide a method for modifying the surface of a particle comprising a magnetic particle.

This object of the present invention can be attained by a method which comprises placing a particle comprising a magnetic particle in a liquid having a monomolecular film formed on its surface, and causing said particle to pass through the air-liquid interface by means of a pair of magnets facing each other with said air-liquid interface being present therebetween, to thereby form a monomolecular coat or a monomolecular built-up coat on the surface of said particle.

DETAILED DESCRIPTION OF THE INVENTION

The present inventor conducted studies in order to develop an effective method for modifying the surface of a bead used in bead agglutination to detect an antigen-antibody reaction in immunoassays. As a result, the present inventor has found that a fine particle such as a plastic bead can be modified to facilitate adhesion of antigens or antibodies by forming a monomolecular coat on its surface.

Figure 1A:
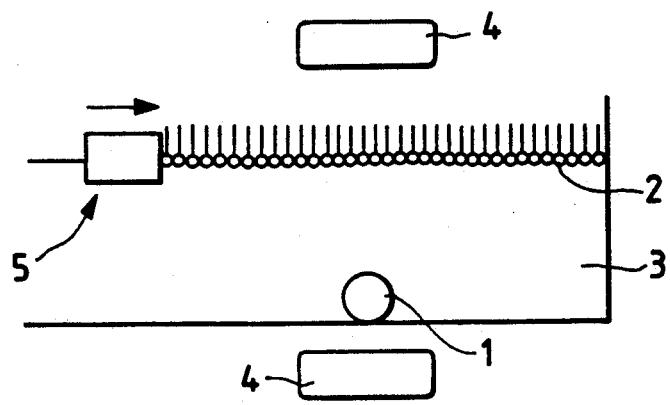
FIGS. 1(a) through 1(c) are diagrams showing how the surface of a particle comprising a magnetic particle is modified by a method of the present invention.
Figure 1B:
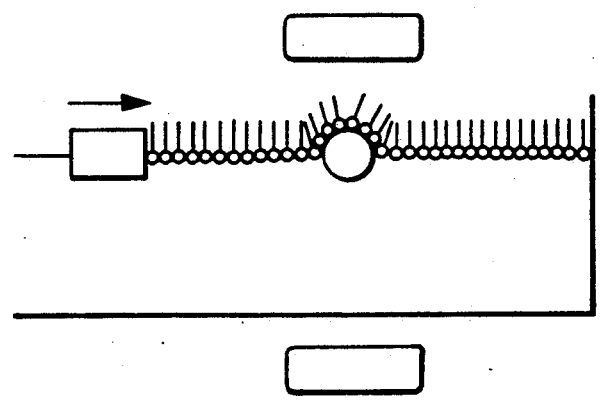
Figure 1C:
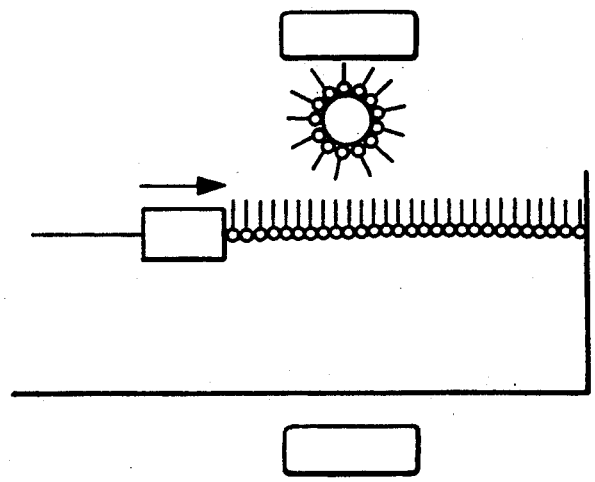

FIGS. 1(a) through 1(c) are diagrams showing how the surface of a particle comprising a magnetic particle is modified by the method of the present invention. In the diagrams, numeral 1 denotes a particle comprising a magnetic particle, 2 is a monomolecular film, 3 is a liquid mass, 4 is a magnet, and 5 is an apparatus for forming a monomolecular film.

The particle 1 comprising a magnetic particle is placed in the liquid 3 having the monomolecular film 2 formed on its surface. Receiving a magnetic force from a pair of magnets 4, the particle 1 is lifted up and passed through the air-liquid interface, as a result of which a monomolecular coat is formed on the surface of the particle 1.

The particle comprising a magnetic particle, the surface of which is to be modified by the method of the present invention, may be a magnetic particle having a coating of an organic high-molecular-weight compound. Typically used is a magnetic particle that has an organic high-molecular-weight compound coated on its surface with emulsion polymerization or some other suitable method.

The magnetic particle needs only be made of a ferromagnetic material such as $\gamma$-iron oxide, chromium oxide ($CrO_2$), etc. The size of the magnetic particle is not limited to any particular value and it may range from a fine particle of a size of about 1 $\mu$m to a coarse particle of the millimeter order.

Either a permanent magnet or an electromagnet may be used, but an electromagnet is preferred since it facilitates the control of the strength of an applied magnetic field and hence the speed at which the magnetic particle is pulled up.

Organic high-molecular-weight compounds that may be coated on the surface of the magnetic particle include polystyrene and polyacrylamide. Silica gel may also be coated on the magnetic particle A monomolecular film may be formed from those compounds which have a structure similar to that of a "surfactant" in that both a hydrophilic portion and a hydrophobic portion are contained in their molecule. Illustrative hydrophilic portions include a carboxyl group and a metal or amine salt thereof, a sulfonic acid group and a metal or amine salt thereof, a sulfonamido group, an amido group, an amino group, an imino group, a hydroxyl group, a quaternary amino group, an oxyamino group, an oxyimino group, a diazonium group, a guanidine group, a hydrazine group, a phosphoric acid group, an aluminic acid group. An illustrative hydrophobic portion is a long-chain alkyl or fluoroalkyl group having about 5–30 carbon atoms, preferably about 10–25 carbon atoms. These alkyl groups may be either straight-chained or branched as long as they have a suitable length. Other exemplary hydrophobic portions include olefinic hydrocarbon groups such as vinylene, vinylidene and acetylene, condensed polycyclic aromatic groups such as phenyl, naphthyl and anthranyl, and chained polycyclic aromatic groups such as biphenyl and terphenyl. These hydrophilic and hydrophobic portions may each be used either on their own or as an admixture. If desired, they may be positioned at both terminals of the molecule or in its center.

Metal complexes having an organic ligand such as organic chelate compounds, inclusion (clathrate) compounds and other compounds may be used as long as they are capable of forming a monomolecular film.

Illustrative organic compounds capable of forming a monomolecular film further include stearic acid, methyl stearate, metal salts of stearic acid, arachidic acid, as well as dye compounds such as rhodamine B derivatives, phthalocyanine-metal complex derivatives, chlorophyll derivatives, cyanine dye derivatives and ruthenium trisbiphridine derivatives. Also used are organic metal compounds including ferrocene derivatives and organic carboxylic acids containing a metal such as tellurium, etc.

In accordance with the present invention, the surface of the particle is modified at the monomolecular level and this enables not only the formation of an ultrathin film but also the control of a microenvironment. The surface of the magnetic particle can be rendered hydrophobic by depositing a monomolecular film in such a way that the hydrophobic portions will be directed into the air. The degree of hydrophobicity or hydrophilicity of the surface can be subtly controlled by selecting an appropriate compound capable of forming a monomolecular film. A particle having high capabilities can be constructed by alternately depositing monomolecular films made of dissimilar compounds.

For instance, the surface of a bead to be used in bead agglutination may be modified with a monomolecular film, and because of the unique hydrophobic environment provided on its surface, an antibody bead having high activity can be produced.

The method of the present invention is applicable to the purpose of modifying the surface of other kinds of particles such as those used in liquid chromatographic filling agents, ion-exchange resins, solid lubricants for magnetic disks, and magnetic recording materials.

The following examples are provided for the purpose of further illustrating the present invention but are in no way to be taken as limiting.

EXAMPLE 1

As shown in FIG. 1(a), polystyrene bead 1 (4.5 $\mu m\phi$) incorporating $\gamma$-iron oxide was submerged in a water vessel equipped with an apparatus 5 for forming a monomolecular film. Then, a mixture of N-[9-(carboxyphenyl)-6-(ethyloctadecylamino)-3H-xanthen-3-ylidene]-N-ethyloctadecamium perchlorate (rhodamine B derivative) and arachidic acid at a molar ratio of 0.5 : 99.5 was added dropwise as a chloroform solution in an amount of $1.0 \cdot 10^{-3}$ M onto the surface of water 3 to form a monomolecular film 2 of said mixture on the water surface.

A pair of electromagnets 4 positioned in such a way that the monomolecular film 2 would lie therebetween were energized, so that the particle 1 was caused to penetrate the air-water interface and then adsorbed onto the surface of the electromagnet 4 above the water vessel. The particle having a monomolecular coat deposited on its surface was again dropped into water 3 and subjected to the same treatment as described above. These procedures were repeated five times to form a monomolecular built-up coat on the surface of the particle 1.

This magnetic particle was dried at 60° C. and examined under a fluorescence microscope. The magnetic particle fluoresced on account of rhodamine B, indicating the formation of the rhodamine B monomolecular coat on its surface.

EXAMPLE 2

A monomolecular built-up coat was formed on the surface of a particle as in Example 1 except that a $\gamma$-iron oxide particle (1 $\mu m\phi$) having no plastic coat was used as a particle and that ethyl stearate was used as a monomolecular film forming material in place of arachidic acid.

In accordance with the present invention, the surface of a particle comprising a magnetic particle can be easily modified by forming a monomolecular film on its surface. By properly selecting the compound from which a monomolecular film is to be formed, the degree of hydrophilicity or hydrophobicity of the particle's surface, the structure of molecular arrangement on the surface, and even its morphology can be changed in a subtle way. Further, a functional particle can be easily produced by selecting dyes, complexes, inclusion compounds and other functional molecules as compounds from which a monomolecular film is to be formed. The surface of beads to be used in bead agglutination to detect an antigen-antibody reaction in immunoassays may be modified by the method of the present invention in such a way that a hydrophobic environment is provided by the arrangement of a monomolecular film, on the surface of beads. Because of this hydrophobic environment, the beads are capable of efficient adsorption of antibodies and contribute to an improvement in the sensitivity and precision of assays.

What is claimed is:

1. A method of modifying a surface of a particle comprising a magnetic particle, comprising the steps of:
    forming a first monomolecular film of a first compound on a surface of a liquid of a second compound;
    submerging said particle comprising a magnetic particle in said liquid of a second compound; and
    pulling out said particle from said liquid of a second compound by applying a magnetic force to said particle so as to cause said particle to pass through an air-film-liquid interface;
    to form a first monomolecular coat of the first monomolecular film of a first compound on the surface of said particle.

2. The method according to claim 1, further comprising the step of repeating a predetermined number of times the submerging and pulling out steps, respectively, to form a built-up coat on the surface of said particle, said built-up film consisting of said predetermined number of layers of said first monomolecular coat.

3. The method according to claim 1, further comprising:
    removing said first monomolecular film of a fist compound from the surface of said liquid of a second compound;
    forming a second monomolecular film of a third compound on the surface of said liquid of a second compound;
    submerging said particle coated with said first monomolecular coat in said liquid of a second compound; and
    pulling out said particle from said liquid of a second compound by applying said magnetic force to said particle so as to cause said particle to pass through an air-film-liquid interface;
    to form a second monomolecular coat of the second monomolecular film of a third compound over said first monomolecular coat on the surface of said particle.

4. The method according to claim 3, wherein said second monomolecular film of a third compound is formed on the surface of a liquid of a fourth compound.

5. The method according to claim 3, further comprising the step of repeating a predetermined number of times the submerging and pulling out steps, respectively, with said second monomolecular film of a third compound on the surface of said liquid of a second compound, to form a built-up coat on the surface of said particle, said built-up coat consisting of said first monomolecular coat and said predetermined number of layers of said second monomolecular coat.

6. The method according to claim 3, further comprising the step of repeating a predetermined number of times the submerging and pulling out steps, respectively, with said first monomolecular film of a first compound and said second monomolecular film of a third compound in alternating manner, to form a built-up coat on the surface of said particle, said built-up coat consisting of a predetermined number of alternating layers of said first monomolecular coat and said second monomolecular coat.

7. The method according to claim 1, wherein said magnetic force is provided by a pair of electromagnets arranged so as to face each other with said air-film-liquid interface being present between said electromagnets.

8. The method according to claim 1, wherein said particle comprises the magnetic particle and a high-molecular-weight compound coated on the surface of said magnetic particle.

9. The method according to claim 1, wherein said first monomolecular film of a first compound on the surface of said liquid of a second compound is formed using a compound having a hydrophilic portion and a hydrophobic portion.

10. The method according to claim 1, wherein said first monomolecular film of a first compound on the surface of said liquid of a second compound is made using a rhodamine B derivative.

* * * * *